(12) United States Patent
Miyajima et al.

(10) Patent No.: US 7,731,656 B2
(45) Date of Patent: Jun. 8, 2010

(54) IMAGE DISPLAY SYSTEM, IMAGE DISPLAY DEVICE, IMAGE DISPLAY METHOD

(75) Inventors: Yasushi Miyajima, Kanagawa (JP); Yoichiro Sako, Tokyo (JP); Toshiro Terauchi, Tokyo (JP); Makoto Inoue, Kanagawa (JP); Katsuya Shirai, Kanagawa (JP); Motoyuki Takai, Tokyo (JP); Kenichi Makino, Kanagawa (JP); Akiko Inoue, Saitama (JP); Masamichi Asukai, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 10/567,930

(22) PCT Filed: Aug. 13, 2004

(86) PCT No.: PCT/JP2004/011707

§ 371 (c)(1),
(2), (4) Date: Feb. 10, 2006

(87) PCT Pub. No.: WO2005/016137

PCT Pub. Date: Feb. 24, 2005

(65) Prior Publication Data

US 2006/0217598 A1 Sep. 28, 2006

(30) Foreign Application Priority Data

Aug. 19, 2003 (JP) ............................. 2003-295482
Apr. 30, 2004 (JP) ............................. 2004-136918

(51) Int. Cl.
*A61B 5/00* (2006.01)
(52) U.S. Cl. ....................................... 600/300; 128/920
(58) Field of Classification Search ................... 600/300, 600/301; 128/903–905, 920
See application file for complete search history.

(56) References Cited

U.S. PATENT DOCUMENTS

| 5,907,291 | A | 5/1999 | Chen et al. |
| 5,956,484 | A * | 9/1999 | Rosenberg et al. ............ 709/203 |
| 6,095,949 | A | 8/2000 | Arai |
| 6,478,736 | B1 * | 11/2002 | Mault .......................... 600/300 |
| 6,817,979 | B2 * | 11/2004 | Nihtila ......................... 600/300 |

(Continued)

FOREIGN PATENT DOCUMENTS

CN 1420466 A 5/2003

(Continued)

*Primary Examiner*—Henry M Johnson, III
*Assistant Examiner*—Kai Rajan
(74) *Attorney, Agent, or Firm*—Oblon, Spivak, McClelland, Maier & Neustadt, L.L.P.

(57) ABSTRACT

In an image display system that displays the condition of a person under measurement in a visible form, the person carries a PDA (10). The PDA (10) includes a bio-sensor (11) to detect bio-information on the person and an environmental information sensor (12) to acquire information on the environment around the person. The PDA (10) sends the acquired information to an image display device (20) which is connected to the PDA (10) via a network (100). The image display device (20) includes a CPU (29) that judges the condition of the person on the basis of bio-information and environmental information, generates an image representing the condition of the person and displays the image on a display unit (23).

32 Claims, 16 Drawing Sheets

U.S. PATENT DOCUMENTS

| | | | |
|---|---|---|---|
| 6,902,513 B1 * | 6/2005 | McClure | 482/8 |
| 7,353,137 B2 * | 4/2008 | Vock et al. | 702/173 |
| 2002/0105427 A1 | 8/2002 | Hamamoto et al. | |
| 2002/0109719 A1 * | 8/2002 | Hata et al. | 345/748 |
| 2002/0197967 A1 * | 12/2002 | Scholl et al. | 455/118 |
| 2003/0233129 A1 * | 12/2003 | Matos | 607/5 |
| 2004/0179038 A1 * | 9/2004 | Blattner et al. | 345/751 |

FOREIGN PATENT DOCUMENTS

| | | |
|---|---|---|
| JP | 10-234030 | 9/1998 |
| JP | 2002-34936 | 2/2002 |
| JP | 2002-282227 | 10/2002 |
| JP | 2002-314715 | 10/2002 |
| JP | 2004-49309 | 2/2004 |
| WO | WO 01/52718 | 7/2001 |
| WO | WO 03/022144 | 3/2003 |

\* cited by examiner

| Area | Corresponding areas | Corresponding body portions |
|------|---------------------|-----------------------------|
| a | (30,0) – (170,60) | Head (0x01) |
| b | (0,70) – (199,130) | Chest (0x02) |
| c | (0,140) – (199,199) | Abdomen (0x04) |
| d | (0,70) – (199,130) | Thigh (0x08) |
| e | (0,140) – (199,199) | Calf (0x10) |

FIG.12

IMAGE DISPLAY SYSTEM, IMAGE DISPLAY DEVICE, IMAGE DISPLAY METHOD

TECHNICAL FIELD

The present invention relates to an image displaying system and method, for displaying the condition of a person under measurement in a visible form on a display device, and an image display device for displaying bio-information on a remote person under measurement in a visible form.

This application claims the priority of the Japanese Patent Application No. 2003-295482 filed in the Japanese Patent Office on Aug. 19, 2003 and Japanese Patent Application No. 2004-136918 filed in the Japanese Patent Office on Apr. 30, 2004, the entireties of which are incorporated by reference herein.

BACKGROUND ART

Generally, a person will have an increased heart rate when he or she is nervous, while having a stable heart rate when he or she is calm. The heart rate is a rhythm of heart contraction, and it is a parameter indicating the condition of a person. Data indicating the conditions of a person include respiration, brain wave, etc. in addition to the heart rate. These data are called "bio data" and utilized as parameters quantitatively indicating the conditions of a person in the fields of medicine and service. Also, environmental information quantitatively indicates ambient conditions such as temperature change, wind strength, etc. around a person. Similarly to the bio-information, the environmental information is utilized to know the conditions surrounding the person.

A typical example of the apparatuses utilizing bio-information and environmental information is proposed in the Japanese Patent Application Laid Open No. 2002-282227 (Patent Document No. 1). The apparatus is to acquire an electrocardiogram of a person in a bathtub and generate an image on the basis of the acquired electrocardiogram. This apparatus acquires an electrocardiogram as bio-information and the bathtub temperature as environmental information. An image varying as the information acquisition progresses is presented to the person under measurement of bio-information, and an electrocardiogram is acquired while the person is enjoying the image being displayed.

The apparatus disclosed in the above Patent Document No. 1 is intended to accurately acquire an electrocardiogram but is limited in kind of bio-information to be acquired and purpose of use. Also, this apparatus is to be used by a person under measurement to know his or her own electrocardiogram, but it cannot be used to inform the condition of the person to other people.

As mentioned above, the bio-information and environmental information are characteristic of the affections, bodily condition, surroundings, etc. of the user. Based on bio-information and environmental information, the condition of a person under measurement can be informed to other people. However, since bio-information is provided as a numerical value, experiences and time are required to understand what the numerical value means. Also, vivid display of acquired information on a person is also a pain to the person under measurement. A camcorder may also be installed on part of the person under measurement or in a corner of an examination room to image the person. In this case, the condition of the person can be known at a glance but such an observation of the person will lead to invasion of his privacy.

DISCLOSURE OF THE INVENTION

It is therefore desirable to overcome the above-mentioned drawbacks of the conventional art by providing an image displaying system and method, for displaying the condition of a person under measurement in a visible form on a display device, and an image display device for displaying bio-information on a remote person under measurement in a visible form.

It is also desirable to provide an image display device, and image displaying system and method, for displaying the condition of a person and environmental condition surrounding the person indefinitely.

According to the present invention, there is provided an image displaying system in which a bio-information acquiring device and image display device are disposed in different places, respectively, and the bio-information acquiring device sends acquired information to the image display device via a network. The image display device generates an image representing the condition of a person under measurement on the basis of the received bio-information and displays the image.

According to the present invention, there is also provided an image display device that receives bio-information sent from a bio-information acquiring device and generates an image representing the condition of a person under measurement on the basis of the received bio-information and displays the image.

According to the present invention, there is also provided an image displaying method in which bio-information on a person under measurement is sent to a remote site and an image representing the condition of the person is generated based on the bio-information.

According to the present invention, an image can be generated based on bio-information on a person under examination and information on the environment surrounding the person and the condition of the person can be displayed on the image display devices at a site remote from the person. According to the present invention, no real image is generated that represents the condition of a remote person is generated but an image is provided which is generated based on the bio-information on the person and environment information around him. So, different from any high-precision images for medical use, the image generated according to the present invention can indefinitely represent the condition of the person under measurement and can be enjoyed. Namely, the image has an improved entertaining property.

According to the present invention, the condition of a person under measurement can be displayed at a site remote from the person and can be known unconsciously at a remote site. Since the image display device indefinitely displays the condition of the person, no invasion will be made of the person's privacy.

These objects and other objects, features and advantages of the present invention will become more apparent from the following detailed description of the best mode for carrying out the present invention when taken in conjunction with the accompanying drawings.

BRIEF DESCRIPTION OF THE DRAWINGS

FIG. 12 shows an example of correspondence tables.

BEST MODE FOR CARRYING OUT THE INVENTION

The image display system according to the present invention includes a bio-information acquiring device. The bio-information acquiring device acquires bio-information on a person under measurement (will also be referred to simply as "person" hereunder) and information on the environment around the person, and supplies the acquired bio-information and environment information to an image display device located remote from the person. The image display device generates an image representing the condition of the person on the basis of the bio-information and environment information, and displays it. The image display system can transmit the condition of a person in a remote place by transmitting bio-information via a network.

Figure 1:
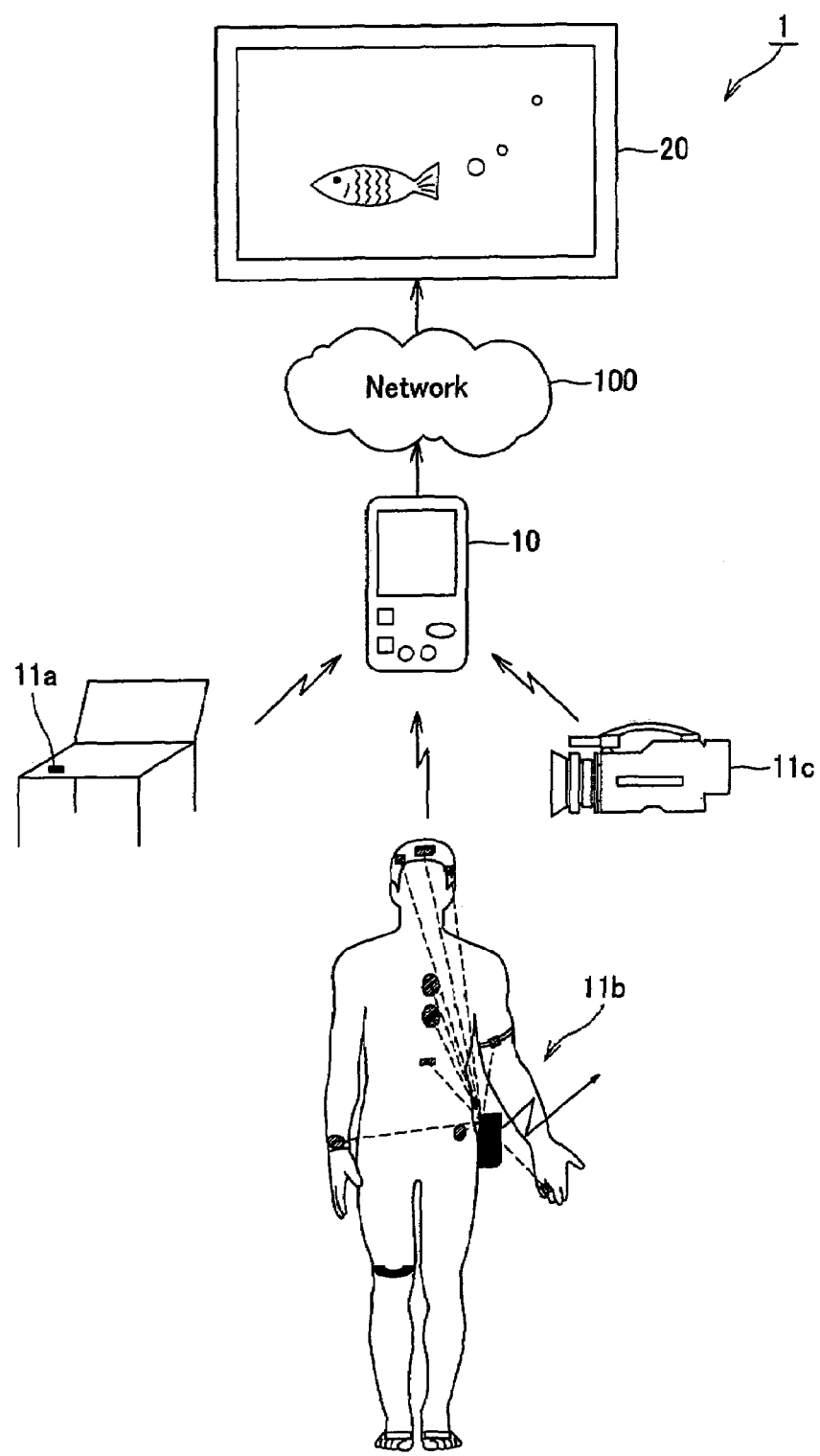
FIG. 1 schematically illustrates the image display system according to the present invention.

The image display system according to the present invention will be described in detail with reference to the accompanying drawings. As shown in FIG. 1, the image display system, generally indicated with a reference numeral 1, includes an electronic bio-information acquiring device 10 connectable to a network (will be referred to as "electronic device" hereunder), and an image display device 20 that receives bio-information acquired by the electronic device 10 and displays it. The electronic device 10 and image display device 20 are connected to each other via a network 100. The network 100 referred to herein is the so-called Internet. The electronic device 10 should desirably be an electronic device that can always be carried, such as a mobile phone, personal digital assistant (PDA) or the like. The electronic device 10 has a bio-sensor provided thereon in a position where the bio-sensor can efficiently acquire bio-information on the device user.

Here will be described an image display system in which the electronic device 10 is, for example, a mobile phone.

Note that the bio-sensor is built in the mobile phone 10 or provided separately from the latter. The bio-sensor separate from the mobile phone 10 is installed on a chair, bed or any other electronic device for direct touch with a part of the person's body. Alternatively, it is put directly on part of the person's body for detection of bio data. The former one is referred to herein as device-touch sensor 11a, while the latter is referred to as body-touch sensor 11b. According to the present invention, a camcorder 11c to image the person and microphone to capture person's voice are included in the bio-sensors.

Figure 2:
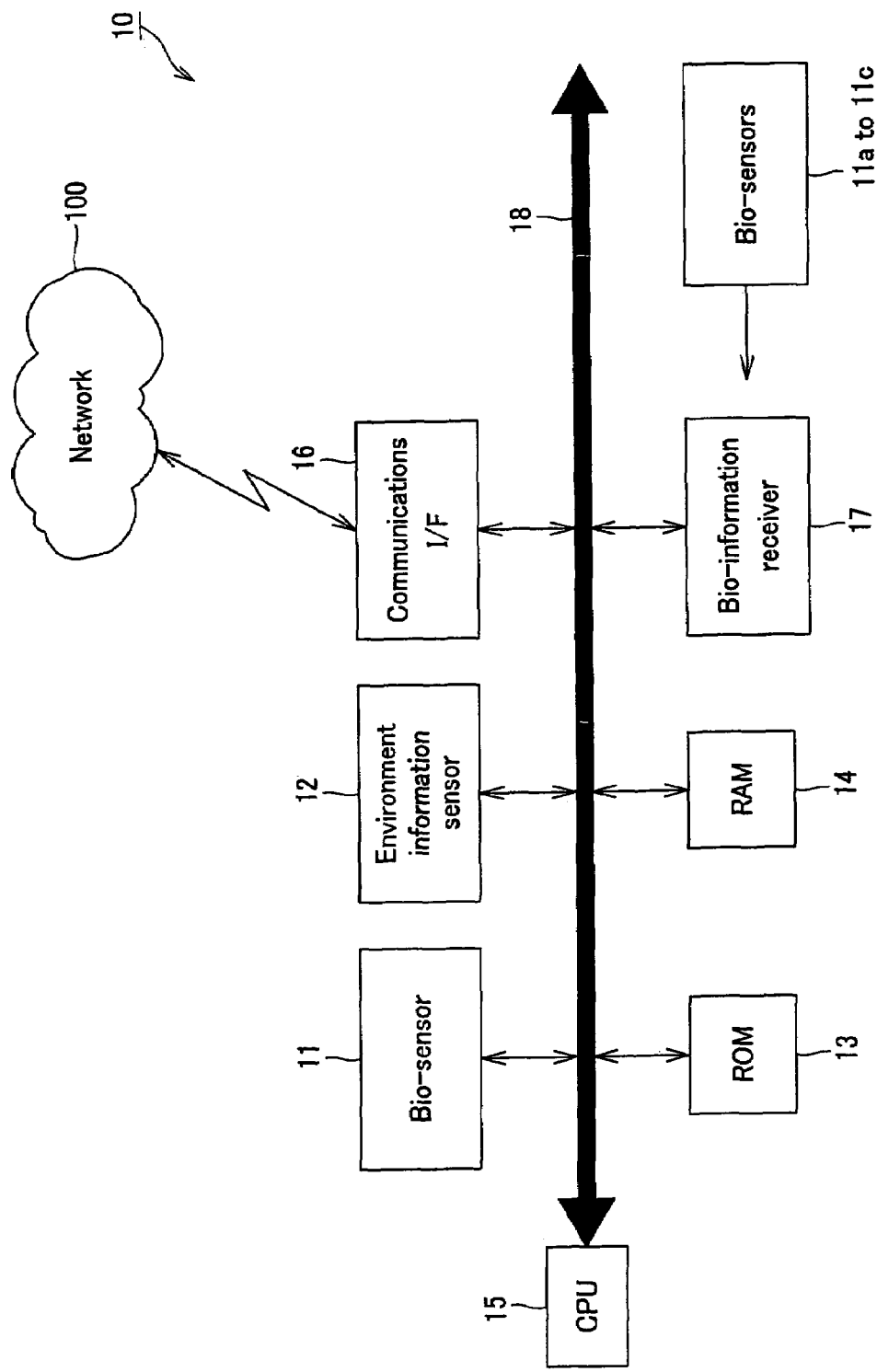
FIG. 2 is a block diagram of a hand-held device or personal digital personal assistant included in the image display system according to the present invention.

The mobile phone or PDA 10 shown in FIG. 2 includes a bio-sensor 11 to acquire bio-information, environment information sensor 12 to acquire environment information, ROM (read-only memory) 13 to store programs, information on settings, etc., RAM (random-access memory) 14 as a provisional storage area, CPU (central processing unit) 15 to make calculation according to the program stored in the ROM 13 and control the mobile phone 10 as a whole, communications interface (I/F) 16 to make data communications according to an internal protocol and a bio-information receiver 17 to receive the bio-information from the external bio-sensor 11. These blocks of the PDA 10 are connected to each other via a bus 18.

The bio-sensor 11 acquired bio-information. The bio-information quantitatively indicates motions of organs of a human body, such as a blood pressure, pulsation, brain wave, etc. The bio-sensor 11 is provided on and in the PDA 10. For example, a clinical thermometer, pulse meter, sudorometer and the like are provided on the PDA 10 at the portion to be gripped most frequently by the user or person. An accelerometer, vibration meter and the like are provided inside the PDA 10. A respirometer is provided at the microphone of the PDA 10.

Also, the bio-sensor 11 is provided in a place remote from the mobile phone 10, such as part of the user's body, furniture or the room. With the bio-sensors being thus installed in such different places, a wider variety of bio-information can be acquired.

The bio-sensors 11b installed at parts of the user's body include a rheometer, electroencephalograph, eye movement sensor, electrocardiograph, oscillation gyroscope, acceleration sensor, skin temperature sensor, body motion acceleration sensor, skin conductivity sensor, pulse meter, blood-pressure meter, respiration sensor, pupil diameter sensor, tilt sensor, blood oxygen saturation sensor, etc. The rheometer emits infrared rays to the user's body and detects reflected infrared rays to measure the blood flow in the brain and blood oxygen level. The electroencephalograph measures the brain waves such as α-wave, β-wave, etc. on the basis of a current flowing through the brain. The eye movement sensor is mounted on the user's head to measure the frequency component of an eyeball movement on the basis of a potential in the head. The electrocardiograph measures the user's heart rate on the basis of a current generated by the cardiac muscle. The oscillation gyroscope measures the breast motion and breathing rate on the basis of an angular velocity. The skin temperature sensor measures the bodily temperature. The skin conductivity sensor measures the sweating rate on the basis of the skin electric resistance. The respiration sensor is wound on the user's chest to detect a voltage variation caused by the respiration. The tilt sensor measures the body posture on the basis of a tilt of each body portion.

Also, the bio-sensors 11a to be provided on a further or floor includes a thermograph, body motion sensor, respirometer, pulse meter, etc. The bio-sensor 11 installed on the sofa, bed or the like extracts a pulse, respiration and body motion on the basis of a pattern of pressure variation caused by the body motion and conveyed via an elastic material on the sofa or bed. The thermograph measures a distribution of the body temperature by means of infrared sensors. The bio-sensors 11c to capture an image and speech of the person include a camcorder and microphone. The camcorder can determine a motion, change of the facial expression, movement of the eye balls. The microphone collects speech of the person. These bio-sensors 11 send bio-information measured by infrared rays or radio to the PDA 10.

The environment information sensor 12 measures information on the environment around the person. The environment information sensor 12 includes a brightness sensor, gas sensor, thermometer, barometer, GPS (global positioning system), etc. The brightness sensor measures the brightness around the person, and gas sensor detects odor. The GPS uses radio waves from a satellite to measure the latitude and longitude of a position where the person exists. The PDA 10 can also acquire environment information via the network 100. Environment information acquired via the network 100 includes weather forecast, lunar age, amount of snow cover, amount of rainfall, atmospheric contamination, wind velocity, etc.

The communications interface 16 sends bio-information acquired by the bio-sensor 11 and environment information acquired by the environment information sensor 12 to the image display device 20. The information sending via the communications interface 16 is controlled by the CPU 15. The CPU 15 executes a program for transmission of bio-information and environment information as a background program, and is triggered by a timer setting to output a sending instruction to the communications interface 16.

The image display device 20 generates an image representing the person's condition on the basis of the bio-information and environment information received from the PDA 10. The image display device 20 may be either a device including a display screen and information processor, such as a TV, mobile phone, personal computer or the like, or a dedicated display device.

Figure 3:
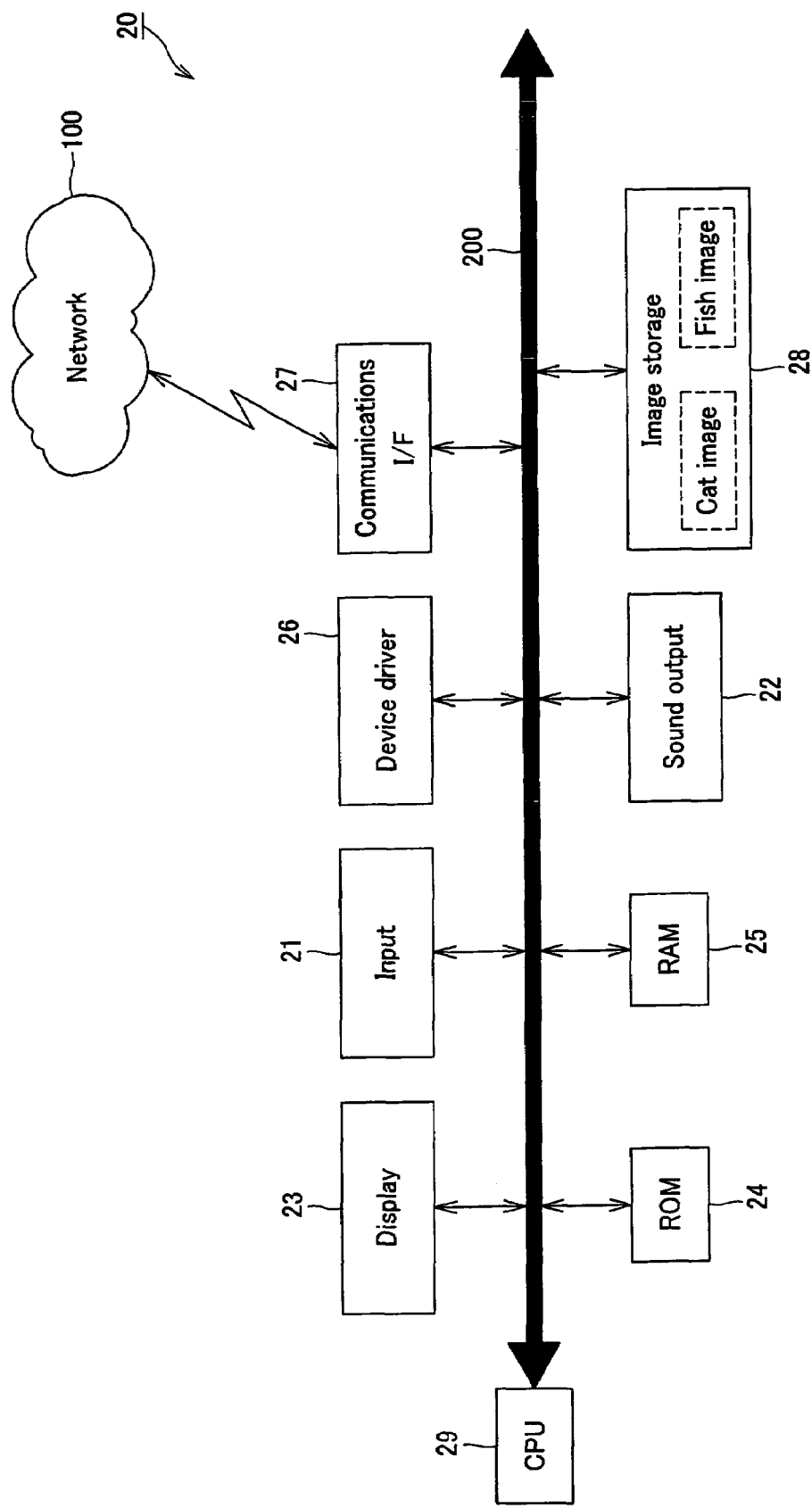
FIG. 3 is also a block diagram of an image display device included in the image display system according to the present invention.

FIG. 3 shows the internal construction of the image display device 20. As shown, the image display device 20 includes an input unit 21 to accept a key-input by the user, sound output unit 22 to provide a speech as an output, display unit 23 to display an image, ROM 24 to store programs and information on settings, RAM 25 as a work area of a CPU 29, device driver 26 to read information from a recording medium, communications interface 27 to make data communications according to a predetermined communications protocol, and an image storage unit 28 to store images. These blocks are connected to each other via a bus 200.

The CPU 29 roughly estimates an emotion and motion of the person on the basis of bio-information to generate an image representing the condition of the person. The image thus generated is resulted from abstraction and symbolization of the person's condition. That is, the image generated by the image display device 20 roughly represents an emotion and motion of the person but does not provide any real representation. According to the present invention, an image of the person is vaguely generated and casually displayed.

An example of the image generation will be explained herebelow. It should be noted that the person is depicted as a fish. The image storage unit 28 stores a program to generate an image from bio-information and environmental information, and a plurality of fish images representing the conditions of the person. The image fishes are, for example, a biting fish, swiftly swimming fish, sleeping fish and the like. Also, the image storage unit 28 has a plurality of background images stored therein. The background images include images of clear water, turbid water, strong flow of water, underwater at night, etc.

The CPU 29 estimates the person's condition from bio-information and environment information to select a fish image that represents the person's state. The method of estimating the person's condition will be explained herebelow. The conditions of a person include emotion such as joy, anger, sorrow and pleasure, sensation such as comfort and discomfort, motions such as eating, moving, sleeping, etc.

The emotion, sensation and motion can be estimated in various manners. For example, emotions such as astonishment fright and uneasiness can be estimated based on a skin electrical resistance. Also, when a person is found to have an elevated heart rate and bodily temperature and his electrocardiogram shows a higher frequency, it can be estimated that he feels "joy". In addition, it is well known that when a person in a mental and psychological stability, he will have a peripheral-vessel dilatation and the arterial blood flow into the peripheral blood vessels so that the heart rate and pulse will change slowly and bodily temperature have a tendency to be higher. Further, in case a person is mentally and psychologically nervous, he will have a peripheral-vessel constriction and the arterial blood flow decrease so that the heart rate and pulse will increase and bodily temperature have a tendency to be lower. Furthermore, it is also well-known that being nervous, a person will have moist hands and differences will occur in value of galvanic skin reflex, heart rate, respiratory cycle amplitude, etc. between when he is in normal state and when he is in nervous state. Also, it has been reported that a person feeling unpleasant will show a larger difference in temperature between the fingertip and palm or between the nose tip and forehead. A method of estimating the emotions such as joy, anger, sorrow and pleasure from brain waves has already been publicized. Emotions such as anger, sorrow, etc. can be evaluated by using, in combination, these physiological indices, facial-expression recognition based on electromyogram representing changes of facial expression and images of the face, posture recognition with the acceleration sensor and tilt sensor, speech recognition, etc.

One example of the method of estimating the emotion, sensation and motion has been explained above. For a more accurate estimation, however, it is of course that a plurality of sensors should desirably be used to acquire a plurality of bio-information.

Next, the estimation of motions will be described. A motion of a person can be estimated based on images captured by, for example, a camcorder. Camcorders are provided on the person's head and at a corner of a room. The CPU 15 can estimate a motion of an object around a person or the person himself on the basis of images captured by the camcorders. A motion of the person can also be estimated from a position where he is. For example, it is highly probable that a person at his office is working, a person in the hospital is feeling sick, a person in the gym is exercising and a person in the restaurant is taking a meal. It is difficult to estimate a person's motion when only positional information on him is available. So, the CPU 15 estimates a person's motion on the basis of a combination of bio-information and environmental information on the person. For example, the CPU 15 estimates a person being in the hospital and having a high bodily temperature to be sick, and a person being in the gym and having the bodily temperature gradually elevated to be sick. Further, the CPU 15 can estimate a person's motion on the basis of sound around the person. In this case, the CPU 15 can estimate an object existing around the person on the basis of the quality and tone interval of the acquired sound and a person's motion by text mining of the person's speech.

As having been explained above, the CPU 29 estimates an emotion, sensation and motion of a person, and then generates images corresponding to the condition of the person. Images can be generated in various manners. For example, a table in which person's conditions and images are associated with each other is stored in the ROM 24 and an image stored in the image storage unit 28 is selected according to the table. Also, an object is generated which outputs an image in response to an input of a person's condition such as emotion, sensation or motion. The image thus generated in any of these manners should evoke a corresponding condition of the person. For example, when the person is taking a meal in the restaurant, an image of a fish which is biting will be generated. When the person feels sick, there will be generated an image of turbid water as background and an image of a fish staying deep in the water. When the person is healthy and active, there will be generated an image of clear water as background and a fish which is swimming swiftly. Also, when it is a fine day, bright underwater will be generated as background. When it is a hot day, there will be generated an image of a fish feeling a little dizzy.

The CPU 29 delicately controls the fish motion, water movement, number and size of bubbles in water, turbid degree of water, etc. This motion control may be done based on a factor independent of bio-information and environmental information. Also, the CPU 29 automatically generates images irrespective of bio-information and environmental information as the case may be. The automatic image generation will be done when the person refuses the measurement of bio-information on him, no bio-information can be made on him or when the CPU 29 cannot receive any bio-information and environmental information because the transmission channel is in trouble.

The CPU 29 controls the display unit 23 to display images thereon. The display unit 23 displays an image representing a condition of the person. It should be noted however that the image is not any real one but a one indefinitely depicting a person's condition. Since the image is an abstract one, it will not deeply intrude on the person's privacy even if it is always displayed but a long-time observation of the image will not be any agony. The display unit 23 displaying a living thing or scenery depicted as such an image may be placed like a photo holding frame or painting frame on the living room wall or furniture. Also, the person's condition can always be known from such an image displayed on the PDA 10.

Figure 4:
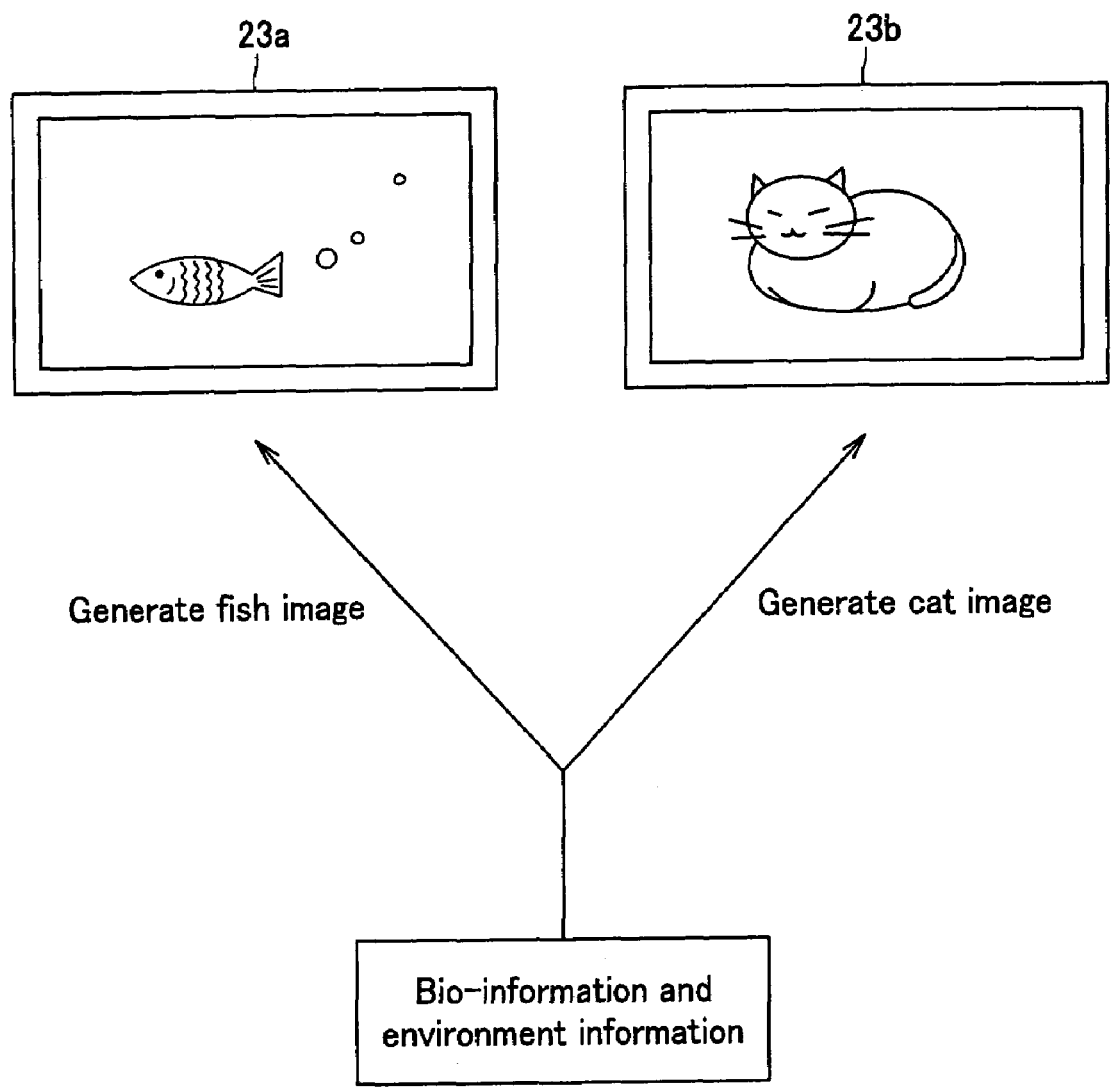
FIG. 4 shows a procedure for generating different images from the same bio-information and environmental information.

The image displayed on the display unit 23 is not limited to a fish but may be a dog, cat or any other living thing, a computer graphics. The image may be displayed simultaneously with an output of a sample sound or synthesized sound from the sound output unit 22. Images can be selected for display. The image storage unit 28 has various images and sounds stored therein. The image display device 20 can selectively change the image from one to another correspondingly to a user's choice. FIG. 4 shows examples of a screen 23a displaying an image of a fish and a screen 23b displaying an image of a cat. These images are different from each other but are generated based on the same bio-information and environmental information. The image displayed may be a real one like a photo or a deformed one like an animation. In any case, the image should be such an image as will evoke a corresponding condition of the person.

The image displayed may be pre-recorded in the image storage device 28 or may be acquired from outside via the network 100 or a recording medium. By acquiring images not stored in the image storage device 28 from outside, it is possible to wide the variation of images that can be displayed and exploit a business of setting such images.

As above, the image display system 1 informs a remote user of a condition of the person. The image representing a person's condition is an indefinite one which will not make the person himself and viewer feel unpleasant. It can broadly represent a person's condition. The image display system 1 provides a system to monitor an old person living in a remote place or a child having gone away from home. Also, the image display system 1 can represent a change of a person's condition with an image not any real one.

The image display system is intended to represent a person's condition by an image and inform a remote user of the person's condition. This image may be provided as an ornamental one that can be used for entertainment.

Figure 5:
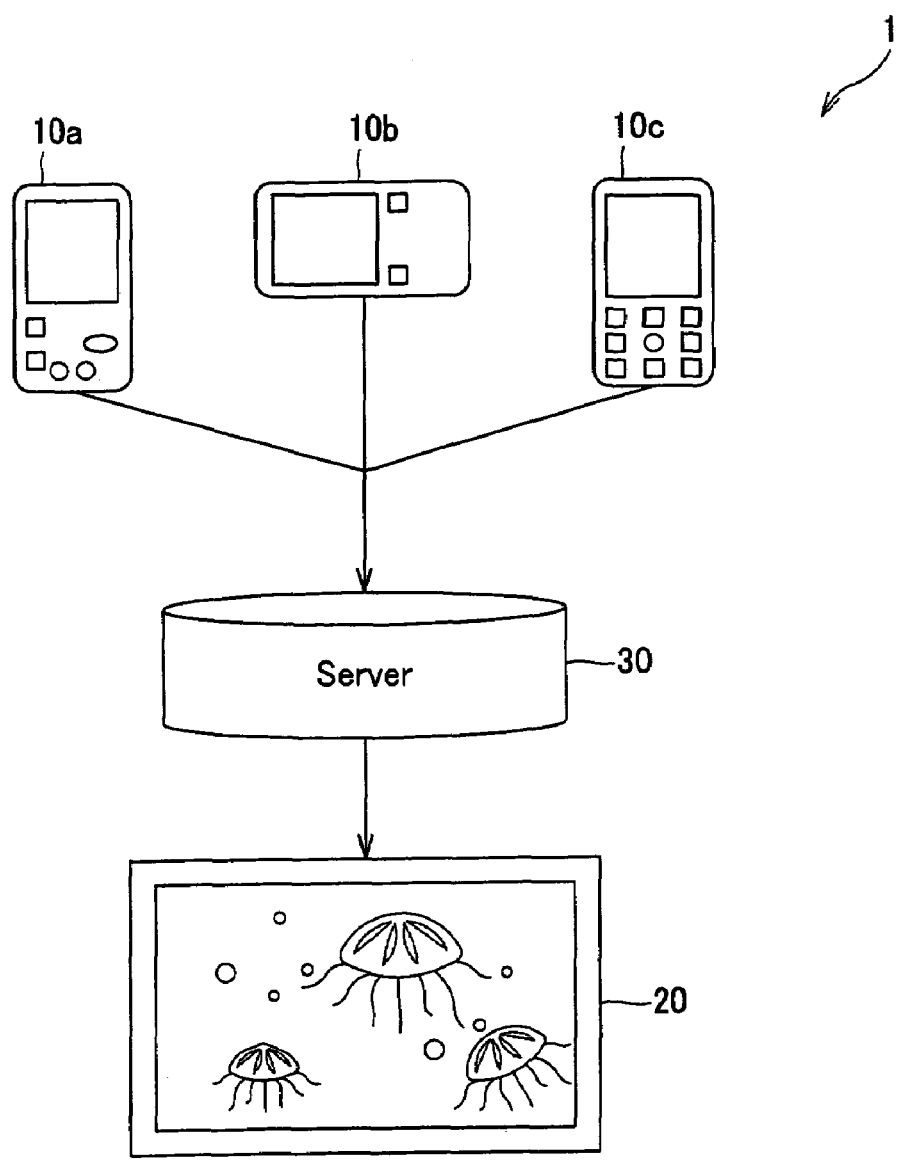
FIG. 5 is a variant of the image display system according to the present invention.

Next, an example of the image display system in which a plurality of images of a person is displayed on a single image display device 20. In this image display system, bio-information and environment information on a person are sent from a plurality of PDAs 10 to a server 30 as shown in FIG. 5. The server 30 multiplexes the bio-information and environmental information received from the PDAs 10 and transfers them to the image display device 20. It should be noted that for sending information on the person to one image display device 20, no server 30 is required.

Figure 6:
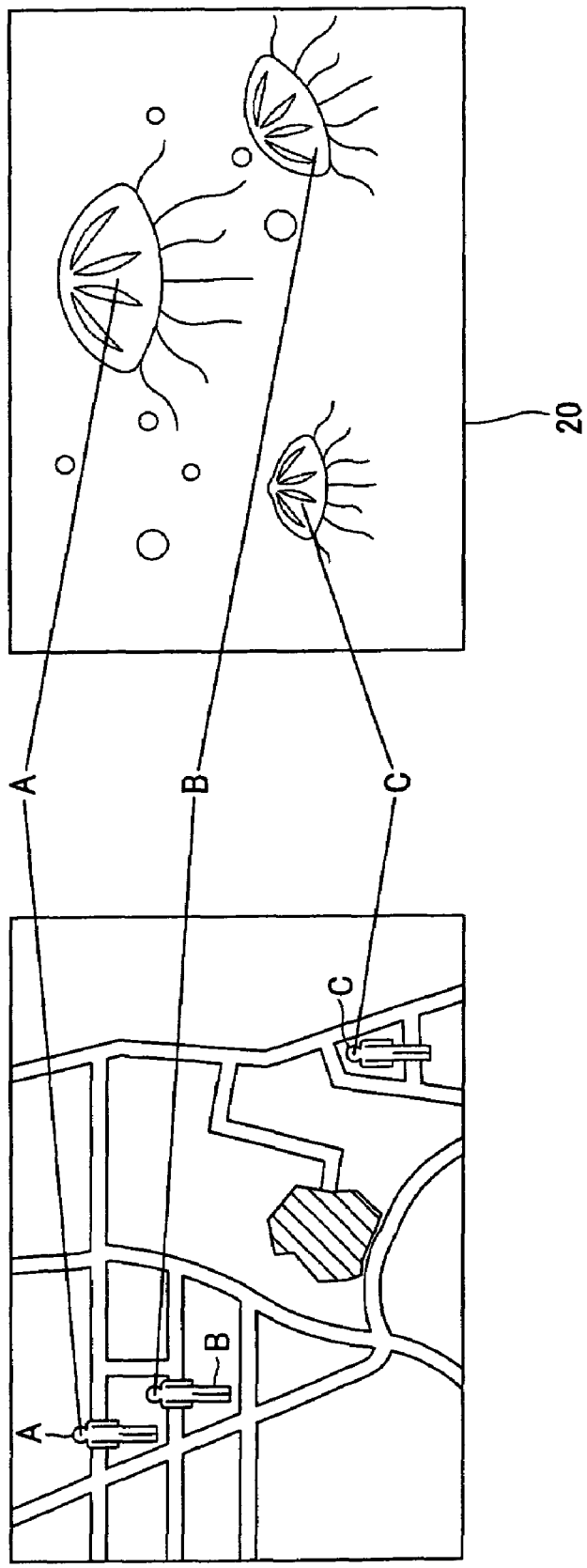
FIG. 6 schematically illustrates an example of images reflecting the physical relation.

The image display device 20 displays an image reflecting the relation among persons. The relation among persons include relation between persons' locations, relation in synchronization between data, relation between environments around the persons, relation between emotions of the persons, etc. The positional information is measured by the GPS. In FIG. 6, positional information on the persons in a map is depicted on a left screen while images reflecting the positional relation are depicted on a right screen. The image display device 20 displays images reflecting the positional information according to a predetermined rule. The rule is stored in the form of a program in the ROM 24 and RAM 25 in the image display device 20. The CPU 29 reads the program and alters the images. In this program, each of the persons is associated with an object, for example, with a jelly fish. Also, objects for persons locating near each other are displayed near each other on the screen. The program determines the object size from the distance between the person and image display device 20. According to this program, the object for the person located near the image display device 20 is displayed on a large scale while the object for the person located away from the image display device 20 is displayed on a small scale.

In the example shown in FIG. 6, the jelly fishes corresponding to the persons A and B, respectively, are positioned near each other and the jelly fish corresponding to the person C is positioned away from the jelly fishes corresponding to the persons A and B. Since the persons A and B are located near the image display device 20, the jelly fishes corresponding to the persons A and B are displayed on the large scale and the jelly fish corresponding to the person C is displayed on the small scale.

The image display device 20 displays images reflecting the relation among the persons and the relation between the persons and itself by applying a simple rule to the positional information on the persons. The persons move independently of each other but their spontaneous motions are associated with each other by applying the rule to the positional information.

Figure 7:
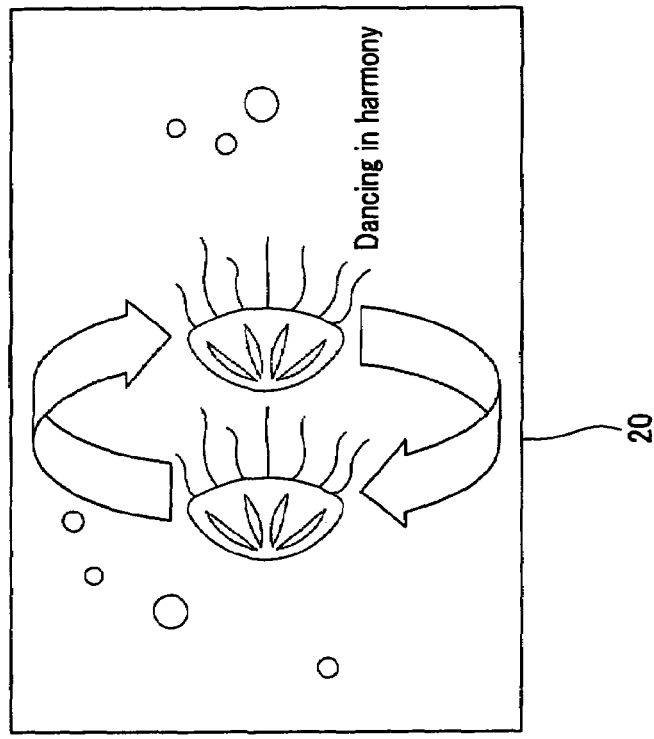
FIG. 7 schematically illustrates an example of images reflecting the relation of synchronization between data.
Figure 7:
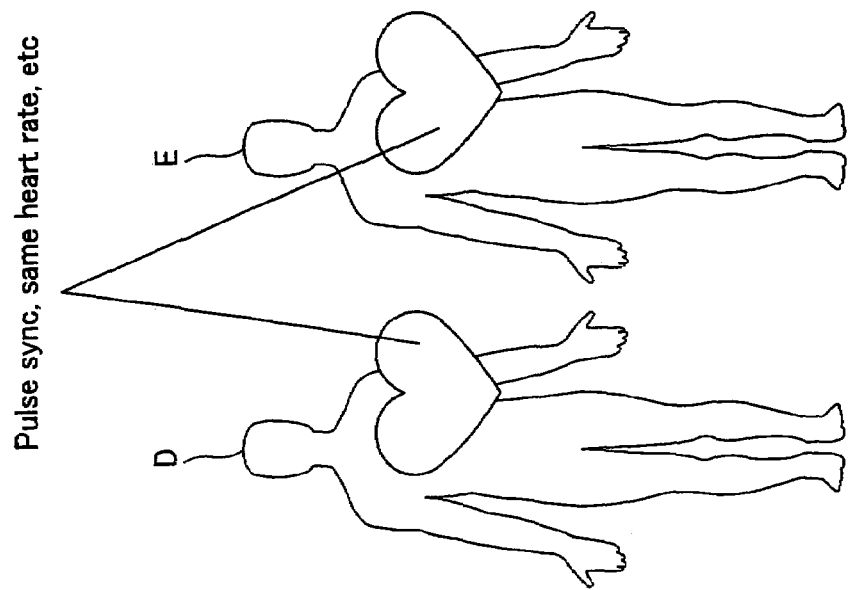

The image display device 20 generates images reflecting the relation of synchronization between data. In this image generation, the image display device 20 refers to the data such as persons' respiration, pulse, walking rhythm, motions, etc. which occur or vary at predetermined intervals. When such data are synchronous with each other by accident, the image display device 20 generates an image indicating the data synchronization. In the left portion of FIG. 7, there is shown the synchronization between the heart rates of persons D and E. Jelly fishes corresponding to the persons D and E are dancing in harmony as shown in the right portion of FIG. 7. For the above, heart rates are entered as input data and a rule to generate a dancing image is applied.

The relation between environments around the person is a difference in environmental information. Environmental information such as brightness, temperature, altitude, weather, etc. can be measured by the environmental information sensor 12. When the ambient temperature around the person varies largely, the image display device 20 will display a jelly fish that moves so violently. When the weather on a location of a person is bad, the image display device 20 will display an image of largely surging waves or turbid water.

Figure 8:
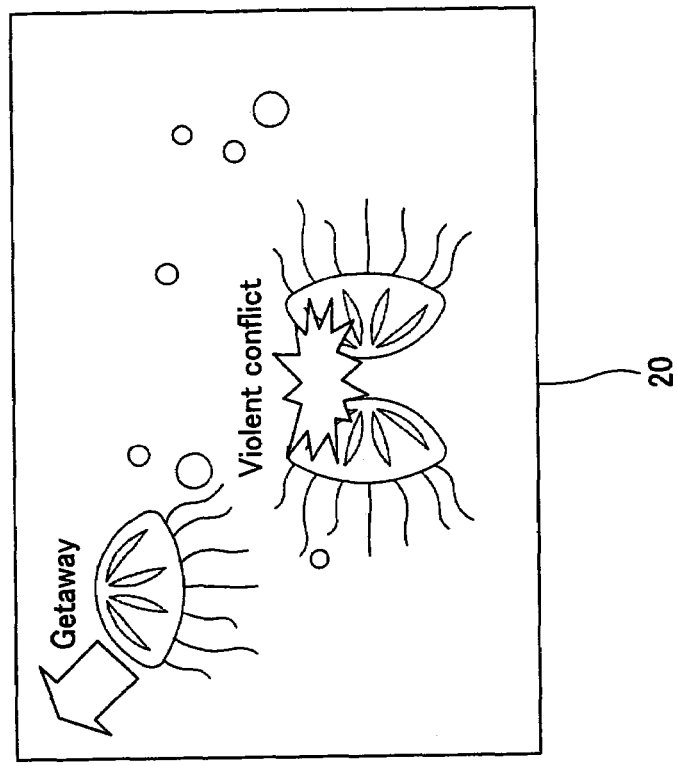
FIG. 8 schematically illustrates an example of images reflecting the affections of a person under measurement.
Figure 8:
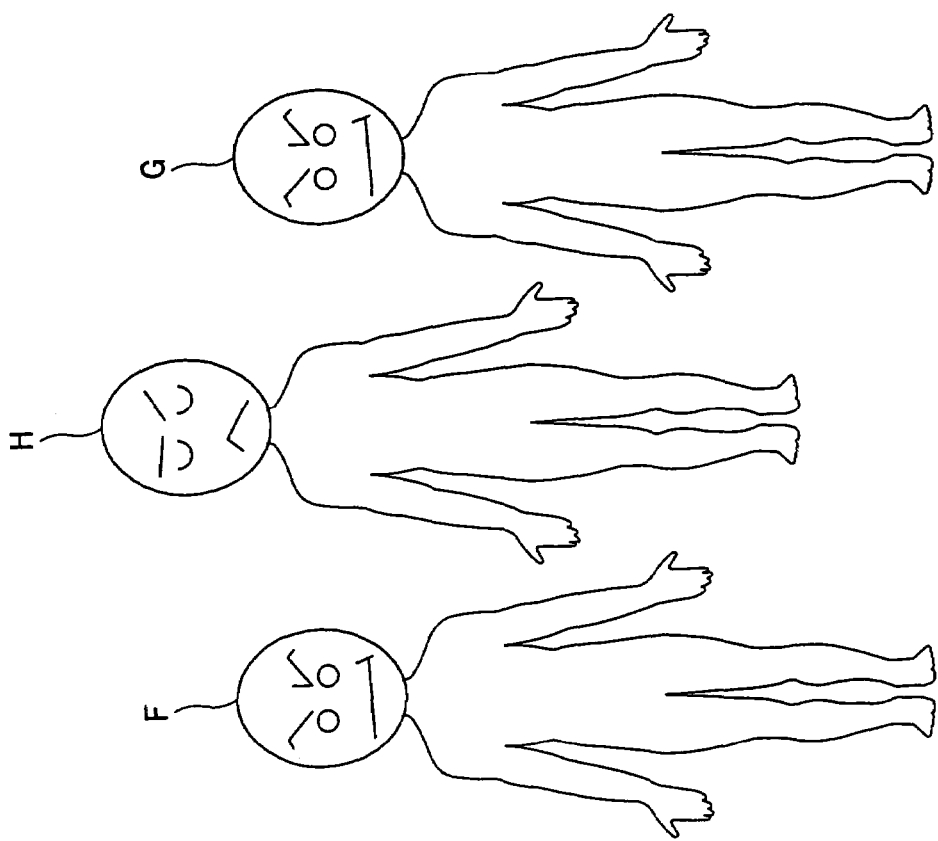

The image display device 20 estimates the emotion and mood of a person from bio-information and environmental information on the person and displays an image reflecting the relation in emotion between the persons. The emotion is estimated as having been described above. FIG. 8 schematically illustrates images reflecting a mood such as pleasantness or unpleasantness. The image display device 20 groups the persons depending upon whether he feels pleasant or unpleasant. Jelly fishes corresponding to the persons belonging to the "pleasant" group are moved in harmony or toward each other, while jelly fishes corresponding to the persons belonging to the "unpleasant" group are put in antagonism with each other, moved away from each other or made to attack each other.

Receiving data on a plurality of persons, the image display device 20 generates images from the relation between the persons. These input data include bio-information and environmental information on the persons. The image display device 20 determines the relation between the persons on the basis of the input data, and stores a program form an image reflecting the relation. The input data, relation and method of generating images reflecting the relation are not limited to any special ones. The present invention proposes a process of determining the relation from the data and generating an image reflecting the relation.

Figure 9:
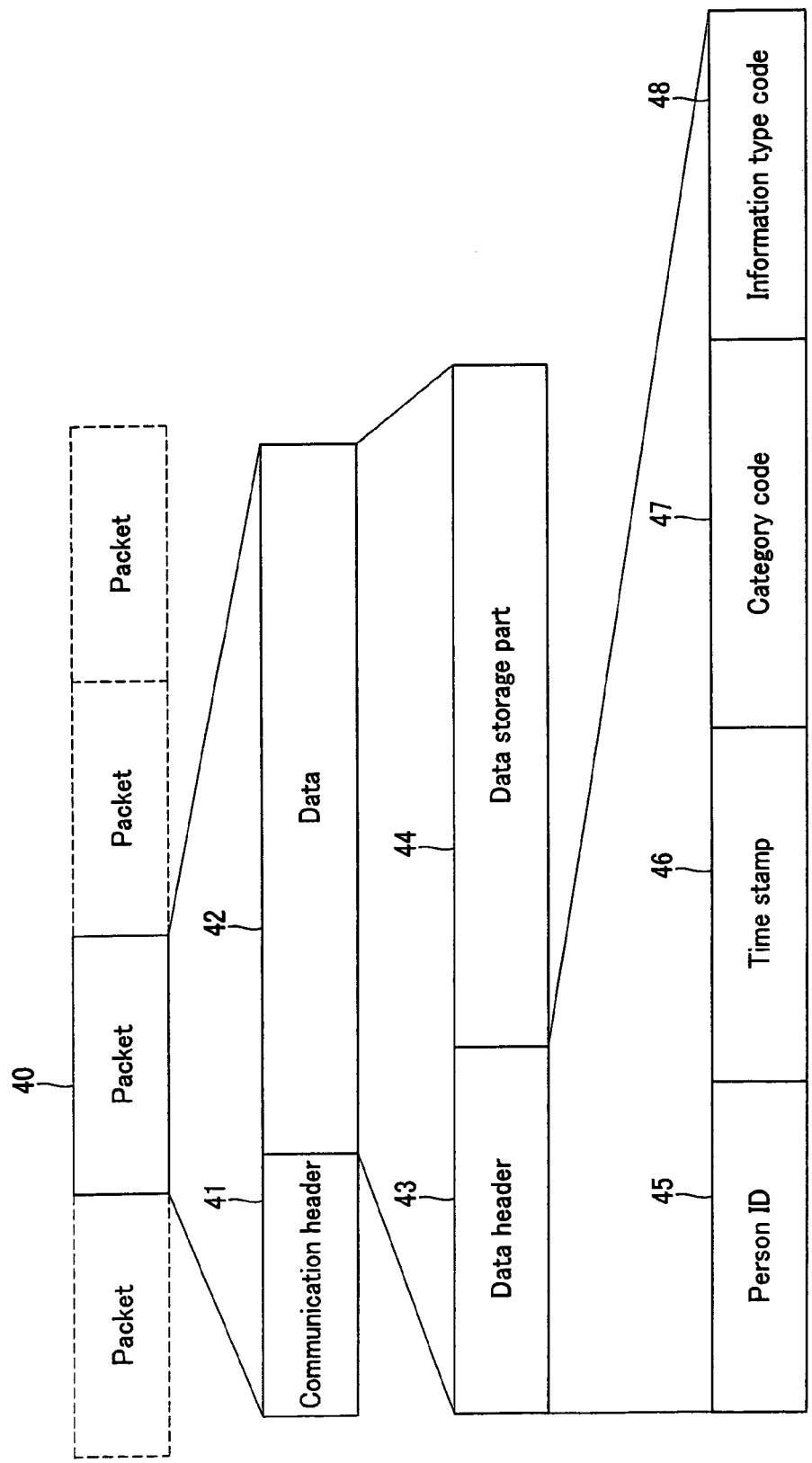
FIG. 9 shows the configuration of multiplexed data.

The data on a plurality of persons is transmitted as will be described below. The server 30 multiplexes data received from the PDA 10. The multiplexed information includes a plurality of packets 40 as shown in FIG. 9. Each of the packets 40 consists of a communication header 41 and data part 42. The communication header 41 stores communication control information such as destination and source addresses. The data part 42 is comprised of a data header 43 and data storage part 44. The data header 43 includes a person ID part 45, time stamp 46 for temporal synchronization, information category code 47 indicative of the category of information, and information type code 48. The information category code 47 indicates which data to be stored in the data storage part 44 is, biological or environmental. The information category code 47 can be extended in case a new information category is measured in future. The information type code 48 indicates which information stored in the data storage part 44 is. For example, a "heart rate", "electromyogram" and "respiration" are indicated with codes "H23", "H24" and "H25", respectively, and a "temperature", "humidity" and "weather" are indicated with codes "K11", "K12" and "K13", respectively.

The data storage part 44 stores an actual value of each time indicated in an information type code 48. For example, for an item "pulse", a numerical value "72" or the like is set in the information type code 48. For item "weather", an actual value or character string indicative of the weather is set in the information type code 48. This field has a variable length. At the top of the data storage part 44, there is set a numerical value indicative of the length of the data storage part itself.

The image display device 20 multiplexes data on the basis of the ID of the person, and then arranges information in a time series on the basis of a time stamp. The image display device 20 generates an image indicating the condition of each person, and displays the generated image on the display unit. In the example of image generation shown in FIG. 5, three persons carry the PDAs 10a, 10b and 10c, respectively, and the three PDAs 10a, 10b and 10c send bio-information and environmental information to the server 30. The server 30 multiplexes the received bio-information and environmental information, and sends the multiplexed information to the image display device 20. The image display device 20 generates images indicating the conditions of the three persons and displays the generated images on the single display unit 23.

Note that although in the aforementioned example, the server 30 is provided as an intermediary device for data transmission, the PDA 10 and image display device 20 may be adapted to make direct data transfer between them without use of the server 30. Also, the configuration of the packet generated by the server 30 and codes of data identifiers are not limited to the above.

In the above example, each of the persons is represented by a pseudo creature, but actually one object or living thing may be represented based on bio-information and environmental information on each person. For example, an engine, tail assembly and main plane of one airplane may be assigned to three different persons, respectively, to represent the airplane being flying. Alternatively, a color, size and bouncing of a ball may be assigned to three different persons to represent the ball being moving.

Next, there will be explained an example in which a viewer of an image and a person under measurement interact with each other. In this example, the viewer gives stimulus to the cutaneous sensation (especially, tactual sensation) of the person. The bio-information on the person is varied due to the stimulus, and the image of the person will be varied due to the variation of the bio-information. In this third embodiment, a feedback loop is established between the person and viewer.

Figure 10:
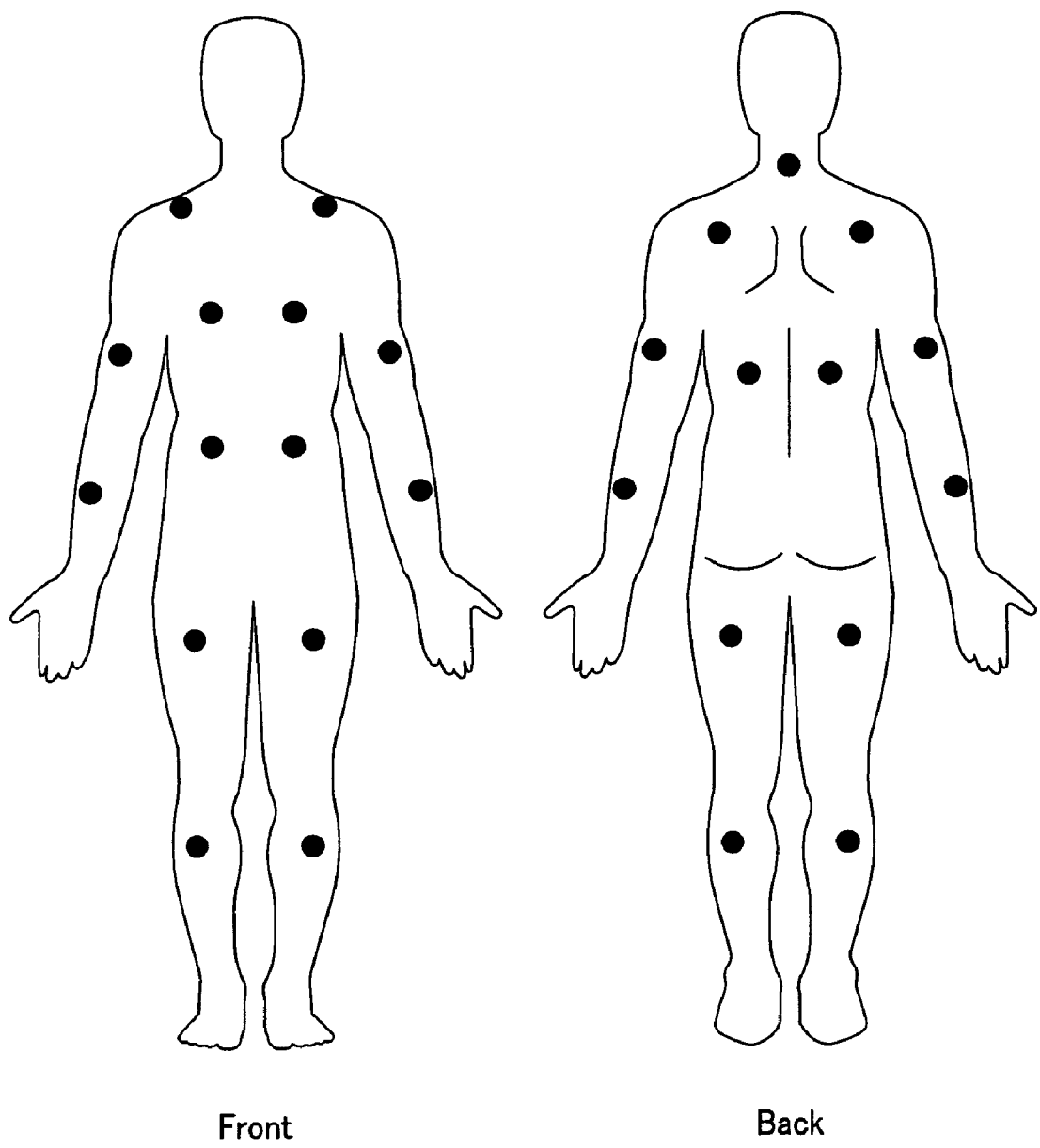
FIG. 10 shows positions where stimulus sensors are located.

Stimulus giving devices 90 are mounted on the person to give stimuli to the skin. In FIG. 10, there are shown mounted locations of the stimulus giving devices 90. The stimulus giving devices 90 are mounted in more than one place on the person's body. Each of the stimulus giving devices 90 converts a touch signal entered at a remote place into physical stimulus. The touch signal is supplied from the PDA 10. The PDA 10 and stimulus giving devices 90 are connected by cable or radio. The stimulus giving device 90 uses at least either vibration by an actuator or motor or electric stimulus used in a low-frequency treatment device to give tactile stimulus to the person. It should be noted that the vibration function of the PDA 10 may be given as stimulus to the person without use of such a special stimulus giving device 90.

The display unit 23 of the image display device 20 includes a touch panel 91. The touch panel 91 may be adapted to detect an input on the basis of a change in resistance or capacitance or it may use a piezoelectric element such as polyvinylidene fluoride (PVDF) or the like. A touch panel adapted to detect an input on the basis of change in resistance or using the piezoelectric element car also detect the strength of tactual sensation.

Figure 11:
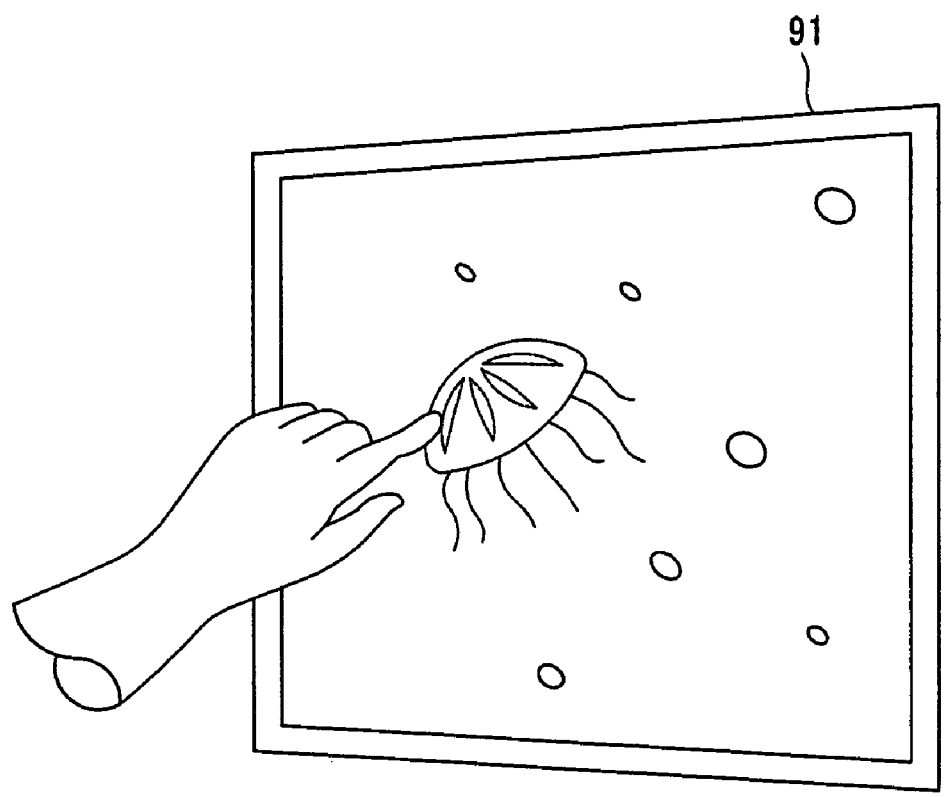
FIG. 11 shows the viewer's touch with a touch panel.

The persons are associated with objects (jelly fishes herein) in an example that will be described below. The display unit 23 displays as many jelly fishes as the persons. Each of the jelly fishes is depicted in one layer. By superposing such layers one on the other, a plurality of jelly fishes is displayed on one display screen. As shown in FIG. 11, when the user touches the touch panel 91 at an object displayed on the display unit 23, the image display device 20 will detect coordinates P of the spot the user has touched. The image display device 20 will make a comparison between coordinates of the object and touched spot to determine whether the spot P is included in that object. The determination is done starting with the deepest layer. When the determination by comparison has finally been done at the front layer, the image display device 20 will determine that the last object determined to include the spot P is the object having been touched by the user.

Figure 13:
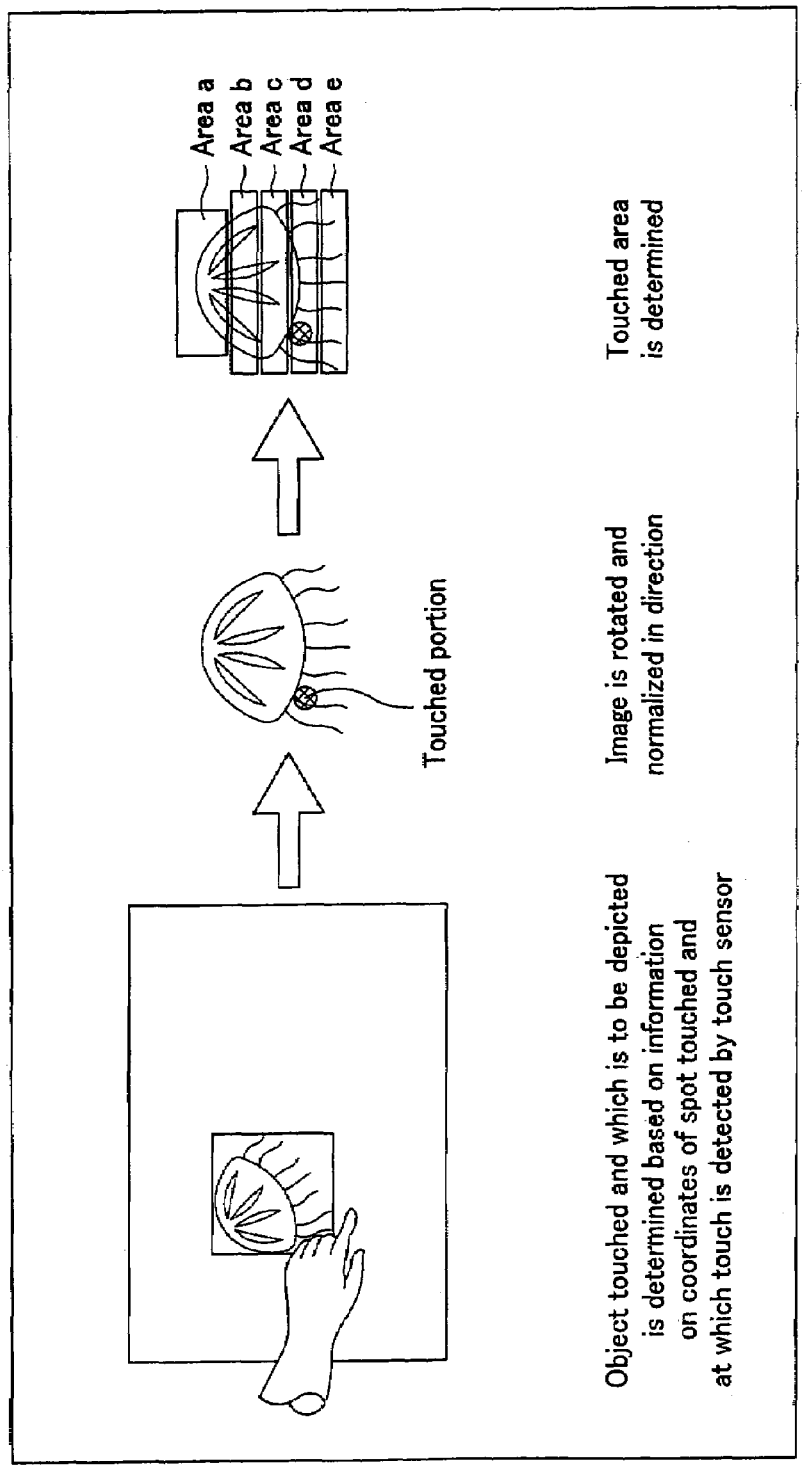
FIG. 13 schematically illustrates a process from the user's touch with the touch panel to identification of an area.

When the touched object is rotating, the image display device 20 will normalize the object. When having determined what the user has touched to be an object, the image display device 20 will determine which portion of the object the user has touched. For this determination, each of the objects is divided into areas. In a correspondence table 92 shown in FIG. 12, there are stored coordinates of the areas and corresponding body portions to which stimulus is to be given. FIG. 13 schematically illustrates a process from touch with the touch panel by the viewer until determination of an area having been touched. Areas a to d correspond to the head, chest, abdomen, thigh and calf, respectively, of the jelly fish. In this example, the spot P touched by the viewer is included in the area d, that is, the thigh.

Note that the correspondence table 92 should desirably be managed along image data which are to be displayed on the image display device 20 with the touch panel 91. In case image data is downloaded from the network to display an image of, for example, a cat, the correspondence table is also downloaded simultaneously. Since a unique code is assigned to each of portions to which tactile stimulus is to be given, so the code for a corresponding portion is always constant whether the display image is a jelly fish or a cat. In this example, the head is assigned a code "0x01", the chest is assigned a code "0x02", . . . . The code for a corresponding portion is the n-th power of two (2), and it is simultaneously applicable to a plurality of tactile stimulus devices. The corresponding portions are in five kinds in this example, but the number of corresponding portions may be limitlessly increased unless the codes are a large load to the system. However, since each of the numerical codes is unique, they should never overlap the existing ones.

Figure 14:
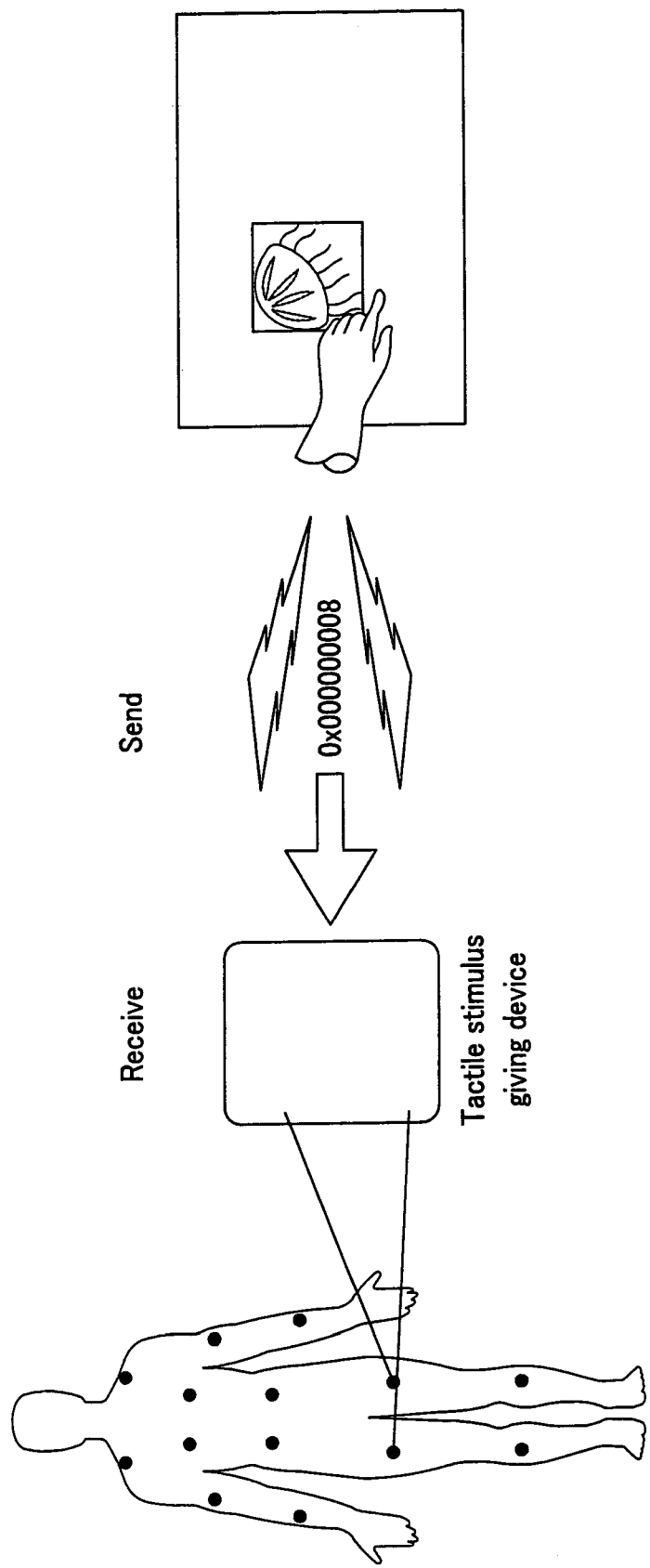
FIG. 14 schematically shows the presentation of a touch with the stimulus sensors from the image display device

When a corresponding portion is determined, the image display device 20 will send, to a remote PDA 10, a touch signal including the code of the corresponding portion, stimulus strength, stimulus type, etc. together. Receiving the touch signal, the PDA 10 drives the stimulus giving device 90 to give physical cutaneous stimulus to the person. FIG. 14 schematically illustrates the transmission of the touch from the image display device 20 to the stimulus giving device 90.

The stimulus type is a code indicating the type of stimulus such as vibration pattern of an actuator, electric stimulus or the like. With this parameter, the vibration frequency of the actuator can be changed, and the vibration rhythm and electric stimulus pattern can be changed. Namely, a variety of stimulus patterns can be given to the person.

Figure 15:
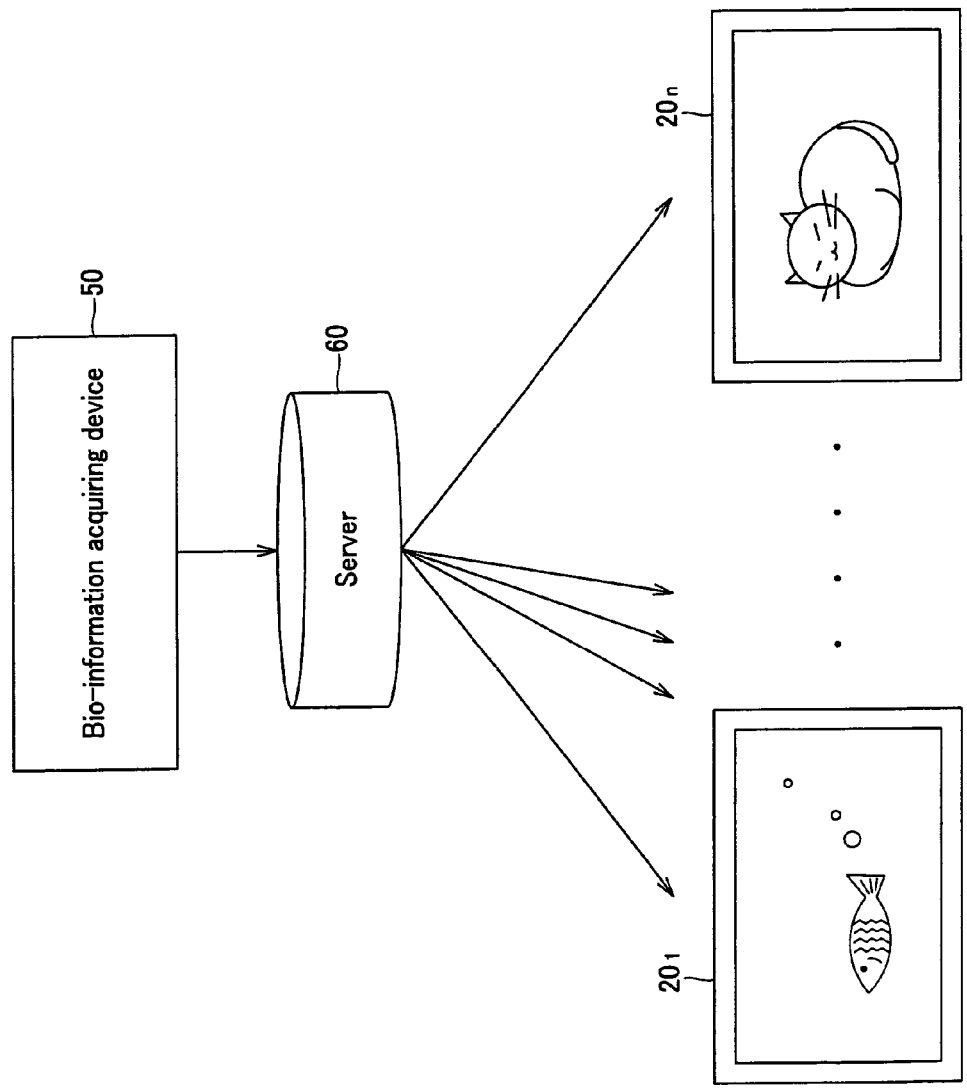
FIG. 15 shows another variant of the image display system according to the present invention.

The image display system 1 may be designed to distribute bio-information and environmental information a specific person under measurement to an unspecified number of image display devices 20. In this case, the image display system 1 includes a bio-information acquiring device 50 to measure bio-information and environmental information on the person, server 60 to send the bio-information and environmental information to many image display devices 20, and an image display device 20 to generate images on the basis of the bio-information and environmental information, as shown in FIG. 15.

The bio-information acquiring device 50 is almost the same in construction as the aforementioned PDA 10. In the image display system 1, since personal information on an individual under measurement is distributed to many other persons, the bio-information acquiring device 50 is not always carried like the PDA but should desirably be installed in a relatively highly public space. Of course, the personal information on the individual may be distributed so if he permits it.

The image display system is used to distribute bio-information and environmental information on a musician playing at a concert or an athlete in action. The distribution of the bio-information and environmental information on the musician or athlete will permit one being at work and not able to actually watch a sports to roughly know the developments of the game and observe changes in emotion of the athlete, which are not viewable by a video replay.

Figure 16:
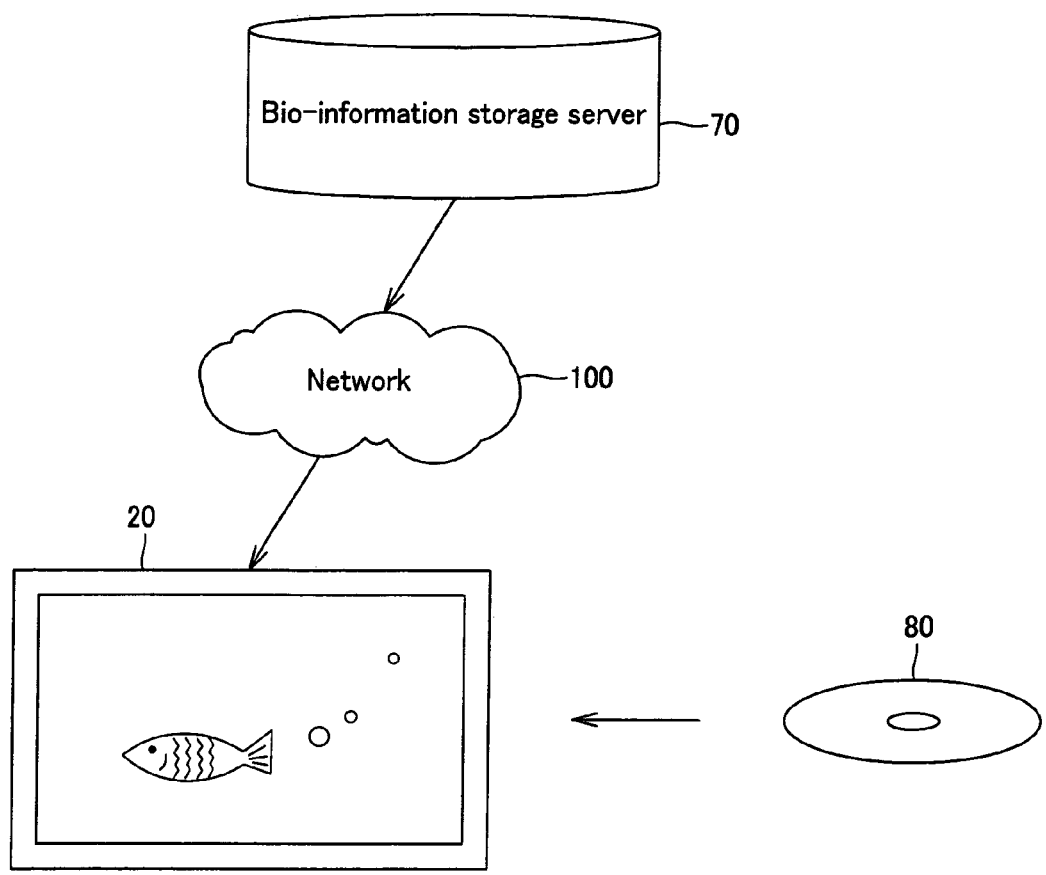
FIG. 16 shows still another variant of the image display system according to the present invention.

Next, there will be described an image display device 20 that is not to reproduce the measured bio-information and environmental information on the real-time basis but to generate images on the basis of bio-information and environmental information already measured. The existing bio-information and environmental information are recorded in a bio-information storage server 70 or a recording medium 80 such as a CD-ROM or semiconductor memory in the network 100, as shown in FIG. 16. The image display device 20 generates images on the basis of these bio-information and environmental information. Thus, the user can enjoy the same image many times. Also, bio-information and environmental information can be measured in advance and displayed any time unless time presses. For example, bio-information on a person can be recorded and his look may be reproduced as a symbol image at any time after his death.

In the foregoing, the present invention has been described in detail concerning certain preferred embodiments thereof as examples with reference to the accompanying drawings. However, it should be understood by those ordinarily skilled in the art that the present invention is not limited to the embodiments but can be modified in various manners, constructed alternatively or embodied in various other forms without departing from the scope and spirit thereof as set forth and defined in the appended claims.

The invention claimed is:

1. An image displaying system, comprising:
a plurality of bio-information acquiring devices including
means for measuring bio-information on each of a plurality of persons under measurement, and
means for transmitting the bio-information; and
an image display device including
receiving means for receiving the bio-information on the plurality of persons under measurement, transmitted from each of the plurality of bio-information acquiring devices,
image generating means for generating an image including objects that interact with each other on the basis of relationships among the bio-information on the plurality of persons under measurement received by the receiving means, and
display means for displaying the generated image,
wherein the plurality of bio-information acquiring devices and the image display device are located in different places and connected to each other via a network.

2. The image displaying system according to claim 1, wherein the image generating means generates an image representing conditions of the plurality of persons under measurement.

3. The image displaying system according to claim 1, wherein the plurality of bio-information acquiring devices include environmental information measuring means for quantitatively measuring environmental information of environments around the plurality of persons under measurement; and
the image generating means generates images representing conditions of the plurality of persons under measurement and the environments around the plurality of persons on the basis of the bio-information and the environmental information.

4. The image displaying system according to claim 3, wherein the image generating means generates images reflecting the relation in the environmental information among the plurality of persons under measurement.

5. The image displaying system according to claim 1, wherein the displaying means generates images of pseudo creatures representing a condition of each of the plurality of persons under measurement, and displays the plurality of pseudo creatures simultaneously.

6. The image displaying system according to claim 1, wherein
the image display device includes touch detecting means for detecting a touch with the displaying means and touch signal sending means for sending a touch signal based on an output from the touch detecting means to one of the plurality of bio-information acquiring devices; and
each of the plurality of bio-information acquiring devices includes a cutaneous-stimulus giving means for giving cutaneous stimulus to one of the plurality of persons under measurement when receiving the touch signal.

7. The image displaying system according to claim 6, wherein the cutaneous-stimulus giving means gives stimulus at least by vibration, electric stimulus and friction.

8. The image displaying system according to claim 1, wherein
the image display device includes read-out means for reading out information recorded in a recording medium; and
the image generating means generates images representing conditions of the plurality of persons under measurement and environments around the plurality of persons on the basis of bio-information and environmental information read by the read-out means.

9. The image displaying system according to claim 1, wherein the image display device includes speech generating means for generating a speech representing conditions of the plurality of persons under measurement on the basis of the bio-information, and speech output means for outputting the speech.

10. The image displaying system according to claim 1, wherein the image generating means generates the image based on a comparison between the bio-information on the plurality of persons under management received by the receiving means.

11. The image displaying system according to claim 1, further comprising:
means for estimating emotions of the plurality of persons under measurement based on the bio-information received by the receiving means, wherein
the image generating means generates the image based on the emotions estimated by the means for estimating.

12. An image display device connected, via a network, to a plurality of bio-information acquiring devices configured to acquire bio-information on each of a plurality of persons under measurement, the image display device comprising:
bio-information receiving means for receiving the bio-information on the plurality of persons under measurement transmitted from each of the plurality of bio-information acquiring devices;
image generating means for generating an image including objects that interact with each other on the basis of relationships among the bio-information on the plurality of persons under measurement received by the bio-information receiving means; and
displaying means for displaying the generated image.

13. The image display device according to claim 12, wherein
the plurality of bio-information acquiring devices include an environmental information measuring means for quantitatively measuring environmental information of environments around the plurality of persons under measurement; and
the image generating means generates images representing conditions of the plurality of persons under measurement and the environments around the plurality of persons on the basis of the bio-information and the environmental information.

14. The image display device according to claim 13, wherein the image generating means generates images reflecting the relation in the environmental information among the plurality of persons under measurement.

15. The image display device according to claim 12, further comprising read-out means for reading out information recorded in a recording medium,
the image generating means generating images representing conditions of the plurality of persons under measurement and environments around the plurality of persons on the basis of bio-information and environment information pre-recorded in the recording medium.

16. The image display device according to claim 12, wherein
he image generating means generates images representing conditions of the plurality of persons under measurement; and
the displaying means displays the images representing the conditions of the plurality of persons under measurement simultaneously.

17. The image display device according to claim 12, wherein
the displaying means includes touch detecting means for detecting a touch with the displaying means, and touch signal sending means for sending a touch signal based on an output from the touch detecting means to one of the plurality of bio-information acquiring devices.

18. The image display device according to claim 12, comprising read-out means for reading out information recorded in a recording medium,
the image generating means generates images representing conditions of the plurality of persons under measurement and environments around the plurality of persons on the basis of bio-information and environmental information pre-recorded in the recording medium.

19. The image display device according to claim 12, wherein the image generating means generates the image based on a comparison between the bio-information on the plurality of persons under management received by the bio-information receiving means.

20. The image display device according to claim 12, further comprising:

means for estimating emotions of the plurality of persons under measurement based on the bio-information received by the bio-information receiving means, wherein the image generating means generates the image based on the emotions estimated by the means for estimating.

21. A method of an image display device for displaying an image, the method comprising:

receiving, by the image display device, via a network, bio-information on each of a plurality of persons under measurement;

generating, by a processor in the image display device, an image including objects that interact with each other on the basis of relationships among the bio-information of the plurality of persons under management received in the receiving; and displaying the image generated in the generating.

22. The method according to claim 21, further comprising:

quantitatively measuring environmental information of environments around the plurality of persons under measurement; and the generating the image comprises generating images representing conditions of the plurality of persons under measurement on the basis of the bio-information and the environmental information.

23. The method according to claim 21, wherein the generating the image comprises generating images representing conditions of the plurality of persons under measurement; and the displaying comprises displaying the images representing the conditions of the plurality of persons under measurement simultaneously.

24. The method according to claim 23, wherein the displaying comprises displaying the images that reflect a relation in environmental information among the plurality of persons under measurement.

25. The method according to claim 21, further comprising:

detecting a touch with the image; and giving cutaneous stimulus to one of the plurality of persons under measurement on the basis of a signal of the touch detected in the detecting.

26. The method according to claim 21, wherein the generating comprises generating the image based on a comparison between the bio-information of the plurality of persons under management received in the receiving.

27. The method according to claim 21, further comprising:

estimating emotions of the plurality of persons under measurement based on the bio-information received in the receiving, wherein the generating comprises generating the image based on the emotions estimated in the estimating.

28. An image displaying system, comprising:

a plurality of bio-information acquiring devices including a bio-sensor configured to measure bio-information on each of a plurality of persons under measurement, and a first communications interface configured to transmit the bio-information; and an image display device including a second communications interface configured to receive the bio-information on the plurality of persons under measurement, transmitted from each of the plurality of bio-information acquiring devices, an image generating processor configured to generate an image including objects that interact with each other on the basis of relationships among the bio-information on the plurality of persons under measurement received by the second communications interface, and a display unit configured to display the generated image, wherein the plurality of bio-information acquiring devices and the image display device are located in different places and connected to each other via a network.

29. The image displaying system according to claim 28, wherein the image generating processor is configured to generate the image based on a comparison between the bio-information on the plurality of persons under management received by the second communications interface.

30. The image displaying system according to claim 28, wherein the system is configured to estimate emotions of the plurality of persons under measurement based on the bio-information received by the receiving unit, and the image generating processor is configured to generate the image based on the emotions estimated by the emotion estimating processor.

31. An image display device connected, via a network, to a plurality of bio-information acquiring devices configured to acquire bio-information on each of a plurality of persons under measurement, the image display device comprising:

a communications interface configured to receive the bio-information on the plurality of persons under measurement transmitted from each of the plurality of bio-information acquiring devices;

an image generating processor configured to generate an image including objects that interact with each other on the basis of relationships among the bio-information of the plurality of persons under measurement received by the bio-information receiving unit; and a displaying unit configured to display the generated image.

32. The image display device according to claim 31, wherein the image generating processor is configured to generate the image based on a comparison between the bio-information of the plurality of persons under management received by the communications interface.

* * * * *